United States Patent [19]

Berry et al.

[11] Patent Number: 5,508,460
[45] Date of Patent: Apr. 16, 1996

US005508460A

[54] METHOD OF SYNTHESIZING ARYLSILANES

[75] Inventors: Donald H. Berry, Dresher, Pa.; Peter I. Djurovich, San Jose, Calif.

[73] Assignee: Trustees of the University of Pennsylvania, Philadelphia, Pa.

[21] Appl. No.: 291,585

[22] Filed: Aug. 15, 1994

[51] Int. Cl.$^6$ ...................................... C07F 7/08
[52] U.S. Cl. ............................ 556/481; 556/445
[58] Field of Search ...................... 556/481, 445

[56] References Cited

U.S. PATENT DOCUMENTS

| | | | |
|---|---|---|---|
| 2,626,266 | 1/1953 | Barry | 556/481 |
| 2,800,494 | 7/1957 | Halvska | 260/448.2 |
| 2,902,504 | 9/1959 | Nitzsche et al. | 556/481 |
| 3,188,336 | 6/1965 | Haszeldine | 260/448.2 |
| 3,334,122 | 8/1967 | Cekada et al. | 556/481 |
| 3,627,801 | 12/1971 | Pierce | 260/448.2 |
| 4,474,976 | 10/1984 | Faltynek | 556/481 |
| 5,032,636 | 7/1991 | Ona | 524/265 |
| 5,041,587 | 8/1991 | Itoh et al. | 556/481 X |
| 5,041,588 | 8/1991 | Caporiccio | 556/413 |
| 5,110,973 | 5/1992 | Caporiccio | 556/488 |
| 5,182,246 | 1/1993 | Fuchikama et al. | 556/481 X |

FOREIGN PATENT DOCUMENTS

| | | |
|---|---|---|
| 2511187 | 8/1967 | Germany. |
| 895592 | 5/1962 | United Kingdom. |
| 1075101 | 7/1967 | United Kingdom. |

OTHER PUBLICATIONS

J. Fluorine Chem., I (1971/72) 203–218.
Applied Polymer Symposium No. 22, 103–125 (1973).
Progress in Organic Coatings, 13 (1985) 297–331.
Macromolecules 1994, 27, 1068–1070.
J. Polymer Science Part A–1, vol. 10 (1972), 947–953.

*Primary Examiner*—Paul F. Shaver
*Attorney, Agent, or Firm*—Duane, Morris & Heckscher

[57] ABSTRACT

An improved method for synthesizing arylsilanes is disclosed. Novel catalysts for use in the method are provided. A method for synthesizing the novel catalysts is also disclosed.

20 Claims, No Drawings

METHOD OF SYNTHESIZING ARYLSILANES

FIELD OF THE INVENTION

This invention relates to a method of making arylsilanes and the catalysts employed thereof.

BACKGROUND

Arylsilanes are commercially available chemicals which are used in a variety of industrial and commercial products.

Only two processes appear to be used currently in industry to manufacture arylsilanes. One such process is described in U.S. Pat. No. 2,380,995 to Rochow et al. The Rochow method requires the use of halogenated phenyl compounds as precursor materials and produces halogenated phenyl byproducts. The byproducts formed by the Rochow process are considered environmentally hazardous materials and constitute a serious waste disposal problem for industry. This poses particularly acute problems with regards to waste disposal and storage of hazardous chemicals in view of today's environmental laws and regulations. The other process is described in U.S. Pat. No. 2,499,561 to Barry. The Barry process results in significant redistribution of the silane starting material, is very unselective as to products, with regards to allowing more than one aryl being attached to a silane or more than one silane being attached to an aryl, and requires undesirably high reaction temperature conditions (300°–350° C.) for synthesizing arylsilanes.

Another disadvantage of the Barry and Rochow processes is that neither allows for the synthesis of arylsilanes with functional groups on the aromatic ring.

Japanese Patent Nos. 01 96,186 and 187 (Tanaka et al.) describe a photolytic method of preparation of arylsilanes from hydrosilane and arene.

Another method of making arylsilanes is by way of utilizing Grignard reagents. However, these reagents are expensive and dangerous for large-scale synthesis.

There therefore remains an unfulfilled need in the art for a method of synthesizing arylsilanes which is free of the disadvantages of the methods described above.

More specifically, there remains a serious need in the art for a method of synthesizing arylsilanes, which does not create environmentally hazardous byproducts. Such a method would therefore advantageously avoid problems with regards to disposal or storage of hazardous wastes. Such a method would also favorably operate at lower temperatures and be more tolerant of different functional groups on the aromatic ring of the arylsilane due to relatively mild reaction conditions.

Further, it would be advantageous if such method for synthesizing arylsilanes was not dependent on photolysis.

Such a method encompassing all these advantages with regard to the synthesis of arylsilanes would constitute a considerable improvement over the existing technology.

SUMMARY OF THE INVENTION

The above-described needs are advantageously and unexpectedly fulfilled by way of the present invention. The invention provides for an improved method of making arylsilanes which addresses the needs described in the art.

The method of the present invention provides for synthesizing an arylsilane by reacting a hydrosilane and an arene in the presence of a hydrogen acceptor and a transition metal catalyst. The reaction thereby forms an arylsilane and a protonated hydrogen acceptor.

The present invention therefore unexpectedly and advantageously provides a method of making arylsilanes.

The method of the present invention advantageously and unexpectedly provides for a method of making arylsilanes, which method does not generate environmentally hazardous byproducts.

The method of the present invention also advantageously and unexpectedly allows for the synthesis of arylsilanes with functional groups on the aromatic ring, needs use no halogenated aromatics during the course of the reaction, and favorably operates at lower temperatures than other methods for synthesizing arylsilanes.

Another aspect of the present invention is a novel organometallic catalyst for use in the method of the present invention. The catalyst of the present invention activates both aromatic and aliphatic C—H bonds, and catalyzes Hydrogen/Deuterium exchange in arylsilanes upon thermolysis in the presence of an arene.

Yet another aspect then of the present invention is a method of making the novel catalysts.

The arylsilanes synthesized by way of the present invention have well-known utilities in a number of industrial applications. For instance, arysilanes are important in the silicone polymer area. Aryl substituents are added to silicones to increase polymer refractive index, modulus, thermal stability, and stability to ultraviolet light, and to decrease reactivity with peroxides. Thus, one may tailor the properties of a silicone polymer for a specific application by using a single monomer containing one or two phenyl or aryl groups (a homopolymer), or by using a mixture of alkyl and aryl-substituted monomers.

Other applications of arylsilanes include sila-drugs, and as sterically hindered protecting groups in organic synthesis.

These and other features, aspects, and advantages of the present invention will become better understood with reference to the following description and appended claims.

DETAILED DESCRIPTION OF THE INVENTION

The method of the present invention provides for synthesizing an arylsilane by reacting a hydrosilane and an arene in the presence of a hydrogen acceptor and a catalyst which is a transition metal catalyst complex. The reaction advantageously forms an arylsilane and a protonated hydrogen acceptor as a byproduct.

The reaction is demonstrated as follows:

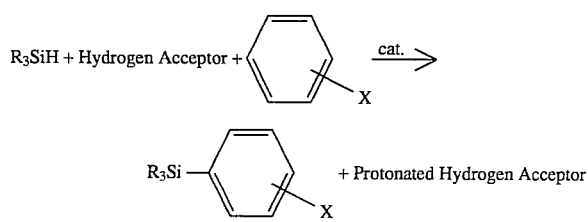

The suitable reactants for use in the method of the present invention are described hereinafter.

The term "silane", as used herein, contemplates those compounds comprising a silicon bonded to other atoms or radicals. They are analogous in terms of nomenclature to known carbon compounds with the exception that silicon is the principal atom instead of carbon.

The invention employs an organosilicon hydride or hydrosilane as the silane reactant. Suitable for use in the present invention is an organosilicon hydride having at least one active Si—H group. The suitable organosilicon hydride or hydrosilane can be represented by the generic formula, $$R_xSiH_y$$

wherein H is hydrogen;
wherein R is a halogen, or a hydrocarbyl or hydrocarbyl derivative selected from the group consisting of an alkyl, alkenyl, alkynl, alkoxy, alkoxyalkyl, halogen-substituted alkyl, halogen-substituted alkenyl, halogen-substituted alkynyl, acyl, acyloxy, alkoxycarbonyl, alkenyloxycarbonyl, alkynyloxycarbonyl, aryl, halogen-substituted aryl, aryloxy, arylalkyl, alkylaryl, halogen-substituted arylalkyl, halogen-substituted alkylaryl, alkoxyaryl, aryloxyalkyl, and the groups being either straight-chained, branched-chained, or cyclo, or combinations thereof, and wherein x=1, 2 or 3;
wherein y=1, 2 or 3 and the sum of x+y=4.
In the preferred embodiment, x=3 and y=1.

Examples of suitable silane compounds include, but are not limited to, trialkylsilanes, such as triethylsilane and trimethlysilane, and dialkylsilane, diarylalkylsilane, diarylsilane, arylalkylsilane, alkylarylsilane, and arylsilanes.

Furthermore, the preferred embodiment encompasses lower alkyl, alkenyl, and alkynl groups having from 1 to 7 carbon atoms. Particularly preferred are trimethylsilane hydride and triethylsilane hydride. The preferred aryl group is phenyl.

Suitable arenes for reaction with the hydrosilanes in theory include all arenes having at least one active C-H group in their ring structure. Suitable arenes are benzene or a substituted benzene of the generic formula:

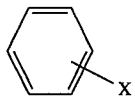

in which single or multiple substitutions may occur in any or all positions on the ring and permutations thereof, and wherein X is either a hydrogen, halogen, or hydrocarbyl or hydrocarbyl derivative selected from the group consiting of an alkyl, alkenyl, alkynl, alkoxy, alkoxyalkyl, halogen-substituted alkyl, halogen-substituted alkenyl, halogen-substituted alkynyl, acyl, acyloxy, alkoxycarbonyl, alkenyloxycarbonyl, alkynyloxycarbonyl, aryl, halogen-substituted aryl, aryloxy, arylalkyl, alkylaryl, halogen-substituted arylalkyl, halgen-substituted alkylaryl, alkoxyaryl, aryloxyalkyl and the groups being either straight-chained, branched or cyclo or combinations thereof.

The preferred arenes for the method of the invention are selected from the group consisting of benzene, chlorobenzene, fluorobenzene, toluene, o-xylene, methoxybenzene (anisole) and napthalene.

Less suitable arenes are those in which the substituents or aliphatic groups contain active hydrogens such as OH and NH. Arenes having such active hydrogens may participate in unproductive side reactions and may compete with the formation of arylsilanes.

The present invention employs a hydrogen acceptor designated as HA herein. The HA bonds with and removes hydrogen from the chemically reactive environment, which results from the catalyzed breaking of the Si—H bond of the hydrosilane, or bonds with other free hydrogen resulting from reactions such as dehydrogenation or elimination reactions.

In theory, any HA is considered suitable in the practice of the present invention. Suitable HAs are those whose kinetics and thermodynamics would favor reaction with hydrogen as opposed to silicon. In the case of unsaturated hydrocarbons, suitable HAs would be those that bond in such manner to the metal of the catalyst complex, so as to reduce back bonding of the π bond with the metal. Such bonding characteristics favorably avoid tight binding of the unsaturated hydrocarbon to the metal, and permit increased reactivity of the unsaturated hydrocarbon.

Suitable HAs are also those unsaturated hydrocarbons which could be described as poor electrophiles. Such poor electrophiles are unsaturated hydrocarbons such as alkenes and alkynes and their derivatives, which are either straight-chained, branched, cyclo or substituted, or combinations thereof.

The preferred HAs are unsaturated hydrocarbons, which are straight-chained or branched in structure as opposed to cyclic. The particularly preferred HAs are those in which the unsaturated carbon bonds are located in an internal position, as opposed to a terminal position on the carbon chain. For example, 2-hexene is such an HA. Also particularly preferred is the structural configuration in which the internal unsaturated carbon bond is in a cis configuration. Furthermore, unsaturated hydrocarbons which are sterically bulky in nature are especially preferred. Such an HA is t-butylethylene.

With regards to less preferred HAs, substituents of the unsaturated hydrocarbons which contain electron-withdrawing groups, such as Si, O, F and CN would also be suitable, but less preferred embodiments due to their electronic properties and potential to react with silicon.

With respect to the catalysts for use in the method of the present invention, suitable catalysts for the method of the present invention have the property of being poor promoters of hydrosilylation reactions due to their chemical kinetics, thermodynamics, or steric properties. These characteristics prevent the consumption of the silane compounds and hydrogen acceptors, which would limit the Si—C bond formation of the arylsilanes and the availability of silane and hydrogen acceptors for such Si—C formations. In addition, catalysts, which constrain the chemical environment for rapid hydrosilylation, provide and promote a chemical environment in which other chemical species can interact with the metal catalytic complex to form arylsilanes. These characteristics may be due in part to steric hinderance which is a consequence of the structure of the metal catalytic complex. Such structural configurations of the catalyst may affect bonding kinetics. However, the inventors do not wish to be bound by any particular mechanism for reactivity.

Suitable catalysts for use in the present invention possess the ability to promote C—H and Si—H bond activation of the arene and hydrosilane compounds, respectively. This activation results in the constructive breaking of the C—H bond of arene and the Si— H bonds of the hydrosilane, and the subsequent formation of a new Si—C bond. In addition, suitable catalysts promote the thermodynamics and kinetics of the reaction in such fashion that the bond activation and breaking of the C—H and Si—H bonds coincide, which favorably results in efficient and selective new Si—C bond formation.

Transition metal catalysts which are well-known in the art are suitable for use in the present invention. Especially suitable are the groups of organometallic catalysts described hereinafter.

Examples of such suitable organometallic catalysts, which exhibit the desirable chemical properties detailed above, are metallic complexes of the general formula:

$$(A)M(H)_{4-x}L_x$$

wherein A is an aromatic, an aromatic derivative or which exhibits aromatic properties, or unsaturated cyclic hydrocarbons and unsaturated cyclic hydrocarbon radicals having between 5 to 10 carbons in their ring structure;

wherein M is a metal such as Fe, Os, Ir, Co, Rh, Ru and other Group VIII metals;

wherein H is hydrogen;

wherein L is a ligand of $SiR_3$;

wherein R is an alkyl, preferably of 1 to 7 carbon atoms; and wherein X is 1, 2 or 3; and $$(B)_3M(H)_{4-x}(L)_x$$

wherein B is an alkyl substituted Group V element such as nitrogen, phosphorus, arsenic, antimony and bismuth, or a carbonyl such as CO;

wherein M is a metal such as Fe, Os, Ir, Co, Rh, Ru and other Group VIII metals;

wherein H is hydrogen;

wherein L is a ligand of $SiR_3$;

wherein R is an alkyl, preferably of 1 to 7 carbon atoms; and wherein X is 1, 2 or 3.

The preferred catalysts in the practice of the present invention are metallic complexes having the general formula:

$$(B)_3M(H)_{4-x}(L)_x$$

wherein B is trimethyl phosphorus;

wherein M is ruthenium;

wherein X=1; and wherein L is a ligand $SiR_3$, wherein R is methyl, and $$(A)M(H)_{4-x}L_x$$

wherein A is an $\eta^6$-arene or arene derivative such as $C_6H_6$, $C_6Me_6$, p-cymene, wherein Me is methyl;

wherein M is ruthenium;

wherein X=2;

wherein H is hydrogen;

wherein L is a ligand of $SiR_3$, and wherein R is methyl or ethyl.

The particularly preferred catalyst in the practice of the present invention is of the formula:

$$(A)M(H)_{4-x}L_x$$

wherein A is a $\eta^5$-cyclopentadienyl group or $\eta^5$-cyclopentadienyl derivative such as cyclopentadienyl, pentamethylcyclopentadienyl;

wherein M is rhodium;

wherein H is hydrogen;

wherein X=2; and wherein L is a ligand of $SiR_3$, and wherein R is either methyl or ethyl.

The catalysts of the present invention include embodiments which additionally provide for substituent groups on the arene and cyclopentadienyl ring structures. Such substituent groups include, e.g. lower alkyls of 1 to 6 carbons and halogens.

The catalysts having the general formula of $(A)M(H)_{4-x}L_x$ are known in the art as four-legged "piano-stool" or half-sandwich structures. In the case of two of the preferred catalysts, the arene-ruthenium and cyclopentadienyl-rhodium complexes, analysis has shown that these structures are isoelectronic analogs which display similar geometry. In particular, where X=2, measurements of the metal-silicon and metal-hydrogen bond lengths and angles of the arene-ruthenium complexes are similar to the values reported for cyclopentadienyl-rhodium complexes as cited in Djurovich et al., *Organometallics*, 13:2551–53 (1994), which is hereby incorporated by reference.

The arene-ruthenium metallic catalyst complexes, which are a new class of catalysts, and the cyclopentadienyl-rhodium catalysts are both unexpectedly superior to traditional catalysts which have little or no reactivity. Traditional catalysts, such as platinum-based complexes, cause rapid hydrosilylation and do not react with arene. Such catalysts are therefore not suitable for practice in the present invention.

The class of cyclopentadienyl-rhodium metallic catalyst complexes are known in the art as described in Fernandez, M.-J.; Maitlis, P. M. *J. Chem. Soc., Chem. Commun.* 1982, 310–311.; Fernandez, M.-J.; Bailey, P. M.; Bentz, P. O.; Ricci, J. S.; Koetzle, T. F.; Maitlis, P. M. *J. Am. Chem. Soc.* 1984, 106, 5458–5463.; Fernandez, M.-J.; Maitlis, P. M. *Organometallics* 1983, 2, 164–165.; Ricci, J. S.; Koetzle, T. F.; Fernandez, M. -J. Maitlis, P. M.; Green, J. C. *J. Organomet. Chem.* 1986, 299, 383–389; Duckett, S. B.; Haddleton, D. M.; Jackson, S. A.; Perutz, R. N.; Poliakoff, M.; Upmacis, R. K. *Organometallics* 1988, 7, 1526–1532; Duckett, S. B.; Perutz, R. N. *J. Chem. Soc., Chem. Commun.* 1991, 28–31, which are incorporated herein by reference.

The cyclopentadienyl-rhodium catalysts are approximately 10–100×more reactive than the arene-ruthenium catalysts in synthesizing arylsilanes in the method of the present invention.

With respect to the reactant phase, catalysts suitable for use in the method of the present invention may be either homogeneous (in solution) or heterogeneous. A suitable heterogeneous catalyst is one in which the catalytically-active transition-metal complex is fixed in place on a solid support member or matrix. The catalyst is reacted with the support or matrix in such fashion as to become intimately associated with such support or matrix. Methods for preparing such heterogeneous catalysts are well-known in the art. Either type of catalyst is considered suitable for industrial synthesis of arylsilanes.

METHOD OF SYNTHESIZING ARYLSILANES

In carrying out the method of the present invention, an equimolar or excess amount of arene is reacted with a hydrosilane in the presence of an HA and a catalytically effective amount of a transition metal complex catalyst. An arylsilane and a protonated HA are formed thereby.

The reaction is carried out at a temperature and for a time sufficient to substantially consume the hydrosilane.

The molar ratio of arene to hydrosilane may range from about 1:1 to 1000:1, though an excess of arene of at least about a 2:1 ratio is preferred to selectively drive the arylsilane reaction, and to avoid the formation of undesirable products. Particularly suitable then may be the use of arene as the solvent to increase the selectivity for arylsilanes by the kinetics of the reaction. Alternatively, one may continually add a 1:1 ratio of silane and HA during the course of the reaction to enhance selectivity. The amounts of the reactants can be varied depending upon the degree or extent of arylsilation desired without undue experimentation. Typically, hydrosilane may be used at a concentration of up to about 10 mol %. Preferably though, the amount of hydrosilane is less than about 5 mol %.

The ratio of hydrogen acceptor to hydrosilane is preferably about equimolar.

An effective amount of the catalyst typically ranges from about 0.1 to about 2 mol %, preferably in a range from about 1 to about 2 mol %.

The reaction may be carried out at a temperature to favorably drive the reaction to produce arylsilane. Typically, this ranges from about 100° C. to about 200° C. More particularly, about 150° C. is suitable.

The reaction may be carried out for a time sufficient to substantially consume the hydrosilane. Reaction time may vary widely and be based upon considerations such as convenience, economy, and catalyst choice, as well as the particular reactants used. The reaction of the present invention may be typically carried out for time ranging from about 2 hours to about 72 hours. The reaction rates of the catalysts have been discussed above. The time of the reaction therefore may then be varied principally depending upon the catalyst utilized.

Typically, the rhodium catalysts, described above, consume about 80% of the hydrosilane in about 2 hours, and a 95% conversion, after about 12 to 14 hours of reaction, is observed. By way of comparison, the ruthenium catalysts require about 48 to 72 hours for similar conversion rates. These reactions were carried out at a temperature of about 150° C.

If so desired, one of skill in the art may also vary the time of the reaction based upon the desired percentage of arylsilane product. For example, reaction time can be shortened if one is satisfied with less than complete conversion of hydrosilane to arylsilane. Since the rate of conversion can be readily monitored and determined, such variations of reaction time are well within the skill of the art. Such variations are a matter of choice and are considered within the scope of the invention.

The reaction is typically carried out in a closed pressure vessel, and loaded in an inert atmosphere, such as under nitrogen, and under normal atmospheric pressure. One of skill in the art, if desired, may decrease or increase the temperature of the reaction, with regards to the above-described temperature range. The temperature can be increased by increasing the pressure as described below. However, too low of a reaction temperature reduces the rate of reaction, while too high of a temperature is not cost effective. Such methods are readily familiar to one of skill in the art.

The reaction may also proceed under elevated or depressed pressures. However, it should be noted that the reaction should not be carried out in an open vessel, since the reaction mixture should not come in contact with atmospheric oxygen which poisons the catalyst. Degassing may be accomplished in various ways known to those skilled in the art. Common methods are purging with nitrogen, or an inert gas such as argon, or subjecting the reaction vessel and its contents to repetitive freeze-pump-thaw cycles. Utilizing either method will allow the reaction to be carried out in an inert environment, thereby preserving the catalyst, and driving the reaction to arylsilane, while avoiding unwanted side reactions or byproducts.

In addition to the desired arylsilane, and protonated HA as byproduct, two additional types of byproducts are generated in significant quantities. These are carbosilanes and hydrosilylation products as discussed hereinafter.

Carbosilanes result from the dehydrogenative coupling of two silane molecules, having the structure $H-SiR_2-CHR-SiR_3$ (e.g., $HSiEt_2CHCH_3SiEt_3$, in the case of the coupling of $HSiEt_3$).

Hydrosilylation products result from the coupling of silane with an alkene, and consist of the simple addition product ($R_3Si-CH_2-CH_2R$) and vinyl silane products ($R_3Si-CH=CHR$).

As for analyzing the results of the reaction, the products of the method of the present invention may be detected by GC/MS analysis by well-known techniques and conditions for such analysis. The desired products, such as the arylsilanes, may be isolated by distillation techniques which are well-known.

With regards to the catalysts, metal silyl complexes may be isolated and also used as catalysts. Alternatively, precursors of the formula $[AMCl_2]_2$, such as [arene-$RuCl_2$ or arene-$RhCl_2]_2$, may be used as catalysts, generating silyls in situ.

Another aspect then of the present invention is a method of making the novel ruthenium catalysts.

As for making the ruthenium catalysts of the present invention, these are synthesized by reacting an appropriate hydrosilane with the corresponding $[(\eta^6\text{-arene}) RuCl_2]_2$.

Typically, the catalysts may be synthesized by reacting excess hydrosilane, such as $Me_3SiH$, with the corresponding $[(\eta^6\text{-arene})RuCl_2]_2$ species, wherein $\eta^6$ is an arene such as $C_6H_6$, $C_6Me_6$ or p-cymene, in THF at about 80° C. for about 12 hours. The reaction is conducted in sealed bombs placed into an oil bath protected behind a safety shield. The product is separated from a black, pyrophoric precipitate by dissolution in hexanes or benzene and filtration through Florisil. The evolved $Me_3SiCl$ is confirmed by NMR and GC, and $H_2$ (0.9 equiv per Ru) is measured by Toepler pump. The benzene derivative can be prepared directly from the reaction of the (p-cymene) ruthenium chloride with $Me_3SiH$ at about 150° C. for about 2 days using benzene as both the solvent and arene source. The catalyst complexes are isolated as colorless, moderately air-stable solids. Confirmation of the structures may be determined by NMR, UV and IR analysis.

The ruthenium catalysts of the present invention are described in further detail in Djurovich et al, *Organometallics*, 13:2551–53 (1994), which, along with all references cited therein, is incorporated herein by reference.

All the other catalysts utilized in the method of the present invention are readily synthesized by methods well-known to those of skill in the art.

For example, the preferred catalysts of formula $$(B)_3M(H)_{4-x}(L)_x$$

are described in Procopio and Berry, *J. Am. Chem. Soc.*, 113:4039 (1991) and Procopio et al., *Polymer Prepr.*, 33(1): 1241 (1992), which are incorporated herein by reference.

The present invention provides an improved method of synthesizing arylsilanes which advantageously and unexpectedly overcomes the shortcomings of the prior art, and further advantageously and unexpectedly provides a cheaper, an environmentally-cleaner and more efficient method for synthesizing arylsilanes.

The following examples are for purposes of further illustrating the present invention and are not to be construed as limiting of the present invention in any fashion whatsoever.

EXAMPLES

Example 1

A mixture of 0.25 g (2.1 mmol) of triethylsilane, 0.18 g (2.1 mmol) tert-butylethylene, 1 mg (0.04 mmol) ($\eta^6$-p-cymene)Ru(SiEt$_3$)$_2$(H)$_2$ were dissolved in 0.95 mL (11 mmol) benzene under a nitrogen atmosphere and stirred at 150° C. in a glass pressure vessel equipped with a Teflon valve. Analysis of the reaction mixture by gas chromatograph after 70 hours revealed that all of the hydrosilane was consumed, and the following compounds produced: phenytriethylsilane (24%), diethyl(1 -triethylsilyl-ethyl)silane (HSiEt$_2$CH(CH$_3$)SiE$_3$) (39%), isomeric hydrosilylation products (20%). The identity of these products was confirmed by $^1$H NMR, gc retention time, gc-mass spectroscopy, and comparison with samples prepared independently by other means.

Example 2

A mixture of 0.25 g (2.1 mmol) of triethylsilane, 0.18 g (2.1 mmol) tert-butylethylene, 29 mg (0.043 mmol) ($\eta^6$-C$_6$Me$_6$)RuCl)$_2$ were dissolved in 4.0 mL (44.8.0 mmol) benzene under a nitrogen atmosphere and stirred at 150° C. in a glass pressure vessel equipped with a Teflon valve. Analysis of the reaction mixture by gas chromatograph after 118 hours revealed that all of the hydrosilane was consumed, and the following compounds produced: phenyltriethylsilane (37%), diethyl (1-triethylsilyl-ethyl) silane (HSiEt$_2$CH(CH$_3$)SiEt$_3$) (49%), isomeric hydrosilylation products (10%).

Example 3

A mixture of 0.25 g (2.1 mmol) of triethylsilane, 0.18 g (2.1 mmol) tert-butylethylene, 13 mg (0.021 mmol) ($\eta^5$-pentamethylcylcyclopentadienyl)RhCl$_2$)$_2$ were dissolved in 5.0 mL (56.0 mmol) benzene under a nitrogen atmosphere and stirred at 150° C. in a glass pressure vessel equipped with a Teflon valve. Analysis of the reaction mixture by gas chromatograph after 20.5 hours revealed that all of the hydrosilane was consumed, and the following compounds produced: phenyltriethylsilane (29%), diethyl(1-triethylsilyl-ethyl)silane (HSiEt$_2$CH(CH$_3$)SiEt$_3$) (34%), isomeric hydrosilylation products (10%).

Example 4

A steel autoclave is charged with a mixture of 52 g (0.45 mol) of triethylsilane, 38 g (0.45 mol) tert-butylethylene, 139 mg (0.15 mmol) ($\eta^5$-pentamethylcyclopentadienyl)RhCl$_2$)$_2$ and 1.0 L benzene under a nitrogen atmosphere and stirred at 150° C. The reaction is monitored periodically by gas chromatograph until all of the hydrosilane is consumed. The contents of the autoclave are transferred to a distillation apparatus, and the compounds are separated by distillation.

Example 5

In this example, a more traditional catalyst ("Wilkinson's Catalyst") is employed. Only hydrosilylation is observed and no arylsilane is produced.

A mixture of 0.25 g (2.1 mol) Rh(PPh$_3$)$_3$Cl were dissolved in 0.96 mL (10.8 mol) benzene under a nitrogen atmosphere and stirred at 150° C. in a glass pressure vessel equipped with a Teflon valve. Analysis of the reaction mixture by gas chromatograph after 22.7 hours revealed that all of the hydrosilane was consumed, and the following compounds produced: phenyltriethylsilane (0%), diethyl (1-triethylsilyl-ethyl)silane (HSiEt$_2$CH(CH$_3$)SiEt$_3$) (1%), isomeric hydrosilylation products (91%).

Although various embodiments of this invention have been illustrated, this was for the purpose of describing, and not limiting the present invention. Various modifications, which will become apparent to one skilled in the art, are considered within the scope of this invention.

What we claim is:

1. A method of synthesizing an arylsilane which comprises reacting a hydrosilane and an arene in the presence of a hydrogen acceptor and a transition metal catalyst, thereby forming an arylsilane.

2. The method of claim 1 wherein the catalyst is of the formula

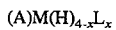

(A)M(H)$_{4-x}$L$_x$ wherein A is an aromatic, an aromatic derivative or which exhibits aromatic properties, or unsaturated cyclic hydrocarbons and unsaturated cyclic hydrocarbon radicals having between 5 to 10 carbons;

wherein M is a metal selected from the group consisting of Fe, Os, Ir, Co, Rh, Ru and other Group VIII metals;

wherein H is hydrogen;

wherein L is a ligand of SiR$_3$;

wherein R is an alkyl, preferably of 1 to 7 carbon atoms; and wherein X is 1, 2 or 3.

3. The method of claim 1 wherein the catalyst is of the formula

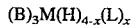

(B)$_3$M(H)$_{4-x}$(L)$_x$ wherein B is an alkyl substituted Group V element such as nitrogen, phosphorus, arsenic, antimony and bismuth, or a carbonyl such as CO;

wherein M is a metal selected from the group consisting of Fe, Os, Ir, Co, Rh, Ru and other Group VIII metals;

wherein H is hydrogen;

wherein L is a ligand of SiR$_3$;

wherein R is an alkyl, preferably of 1 to 7 carbon atoms; and wherein X is 1, 2 or 3.

4. The method of claim 2 wherein the catalyst is of the formula

(A)M(H)$_{4-x}$L$_x$ wherein A is a $\eta^5$-cyclopentadienyl group or $\eta^5$-cyclopentadienyl derivative selected from the group consisting of cyclopentadienyl, pentamethylcyclopentadienyl;

wherein M is rhodium;

wherein H is hydrogen;

wherein X=2; and wherein L is a ligand of SiR$_3$, and wherein R is methyl or ethyl.

5. The method of claim 2 wherein the catalyst is of the formula $(A)M(H)_{4-x}L_x$ wherein A is an $\eta^6$-arene or arene derivative selected from the group consisting of $C_6H_6$, $C_6Me_6$, and p-cymene;

wherein Me is methyl;

wherein M is ruthenium;

wherein X=2;

wherein H is hydrogen;

wherein L is a ligand of $SiR_3$; and wherein R is methyl or ethyl.

6. The method of claim 3 wherein the catalyst is of the formula $(B)_3M(H)_{4-x}(L)_x$ wherein B is trimethyl phosphorus;

wherein M is ruthenium;

wherein X=1; and wherein L is a ligand of $SiR_3$, and wherein R is methyl.

7. The method of claim 1 wherein the hydrosilane is a trialkylsilane selected from the group consisting of trimethylsilane hydride and triethylsilane hydride.

8. The method of claim 1 wherein the arene is selected from the group consisting of benzene, chlorobenzene, fluorobenzene, toluene, o-xylene, methoxybenzene and napthalene.

9. The method of claim 8 wherein the arene is benzene.

10. The method of claim 1 wherein the hydrogen acceptor is an unsaturated hydrocarbon having a double or triple bond.

11. The method of claim 10 wherein the unsaturated hydrocarbon is linear or branched.

12. The method of claim 11 wherein the hydrogen acceptor is selected from the group consisting of t-butylethylene and 2-hexene.

13. The method of claim 1 wherein the reaction is carried out at a temperature of about 100° C. to about 200° C.

14. The method of claim 13 wherein the reaction temperature is about 150° C.

15. The method of claim 1 wherein the reaction is carried out for about 2 hours to about 72 hours.

16. The method of claim 15 wherein the reaction is carried out for about 12 to about 14 hours.

17. The method of claim 1 wherein the catalyst is a precursor catalyst of the formula $(AMCl_2)_2$.

18. The method of claim 1 wherein the catalyst is homogeneous or heterogeneous.

19. The method of claim 12 wherein the hydrogen acceptor is 2-hexene.

20. The method of claim 12 wherein the hydrogen acceptor is t-butylethylene.

* * * * *